(12) United States Patent
Bayer

(10) Patent No.: US 10,327,890 B2
(45) Date of Patent: Jun. 25, 2019

(54) THERMOCHEMICALLY TREATED MINIATURE TUBES AS SEMIFINISHED PRODUCTS FOR VASCULAR STENTS

(71) Applicant: BIOTRONIK AG, Buelach (CH)

(72) Inventor: Ullrich Bayer, Bad Doberan (DE)

(73) Assignee: BIOTRONIK AG, Buelach (CH)

( * ) Notice: Subject to any disclaimer, the term of this patent is extended or adjusted under 35 U.S.C. 154(b) by 286 days.

(21) Appl. No.: 14/565,681

(22) Filed: Dec. 10, 2014

(65) Prior Publication Data

US 2015/0202042 A1 Jul. 23, 2015

Related U.S. Application Data

(60) Provisional application No. 61/929,985, filed on Jan. 22, 2014.

(51) Int. Cl.

| | | |
|---|---|---|
| *A61F 2/24* | (2006.01) | |
| *B05D 3/12* | (2006.01) | |
| *B05D 5/00* | (2006.01) | |
| *C21D 6/00* | (2006.01) | |
| *C21D 7/12* | (2006.01) | |
| *C21D 9/08* | (2006.01) | |
| *C22F 1/06* | (2006.01) | |
| *C22F 1/10* | (2006.01) | |
| *A61L 27/50* | (2006.01) | |
| *A61L 31/14* | (2006.01) | |
| *B21D 26/033* | (2011.01) | |

(52) U.S. Cl.
CPC .............. *A61F 2/24* (2013.01); *A61L 27/50* (2013.01); *A61L 31/14* (2013.01); *B05D 3/12* (2013.01); *B05D 5/00* (2013.01); *B21D 26/033* (2013.01); *C21D 7/12* (2013.01); *C22F 1/06* (2013.01); *C22F 1/10* (2013.01); *C21D 6/004* (2013.01); *C21D 9/08* (2013.01); *Y10T 428/1338* (2015.01); *Y10T 428/1345* (2015.01)

(58) Field of Classification Search
CPC ...... B21D 51/36; B21D 31/04; B21D 26/033; B21D 26/035; B21D 26/041; C21D 7/12; C21D 9/08; A61F 2/24; A61L 27/50; A61L 31/14; B05D 3/12; C22F 1/06; C22F 1/10; Y10T 428/1338; Y10T 428/1345
USPC ...................................... 72/58, 59, 61, 62, 63
See application file for complete search history.

(56) References Cited

U.S. PATENT DOCUMENTS

| | | | | |
|---|---|---|---|---|
| 3,751,954 A | * | 8/1973 | Ezra | B21C 37/06 29/421.2 |
| 5,671,629 A | * | 9/1997 | Valyi | B21D 26/049 72/58 |

(Continued)

FOREIGN PATENT DOCUMENTS

| | | | | |
|---|---|---|---|---|
| DE | 102006035239 | * | 6/2007 | ........... B21D 26/041 |
| JP | 05077026 A | * | 3/1993 | |

OTHER PUBLICATIONS

EP15150399 European Search Report dated Aug. 25, 2015.

*Primary Examiner* — Gregory D Swiatocha
(74) *Attorney, Agent, or Firm* — Wagenknecht IP Law Group PC

(57) ABSTRACT

A method for increasing the fatigue strength of a tubular semifinished product for a medical implant, a tubular semifinished product for a medical implant having improved fatigue strength, and a medical implant produced from such a semifinished product.

6 Claims, 2 Drawing Sheets

(56) References Cited

U.S. PATENT DOCUMENTS

| | | | | |
|---|---|---|---|---|
| 6,006,429 A * | 12/1999 | Hanisch | B23P 11/00 | 29/888.1 |
| 6,266,991 B1 * | 7/2001 | Kuo | B23P 9/025 | 72/370.07 |
| 7,141,060 B1 * | 11/2006 | Metz | A61B 17/11 | 606/194 |
| 8,043,553 B1 * | 10/2011 | Durcan | B29C 43/10 | 264/235 |
| 8,202,477 B2 * | 6/2012 | Papirov | A61L 29/02 | 420/402 |
| 2003/0106698 A1 * | 6/2003 | Simpson | E21B 23/00 | 166/382 |
| 2008/0001333 A1 * | 1/2008 | Kleine | A61F 2/91 | 264/564 |
| 2008/0221664 A1 * | 9/2008 | Bales | A61F 2/88 | 623/1.22 |
| 2008/0318714 A1 * | 12/2008 | Kotula | B21D 26/033 | 473/513 |
| 2011/0120585 A1 * | 5/2011 | Hur | B21D 26/02 | 138/140 |
| 2011/0288630 A1 | 11/2011 | Blanzy | | |
| 2012/0046739 A1 * | 2/2012 | von Oepen | A61F 2/915 | 623/2.11 |
| 2012/0215301 A1 * | 8/2012 | Papirov | A61L 27/047 | 623/1.42 |
| 2013/0218292 A1 * | 8/2013 | Bayer | C10M 103/04 | 623/23.64 |
| 2013/0345688 A1 * | 12/2013 | Babkin | A61B 18/02 | 606/20 |
| 2015/0343519 A1 * | 12/2015 | Colosseo | F16C 3/02 | 29/888.1 |
| 2016/0052045 A1 * | 2/2016 | Mizumura | F01L 1/047 | 29/888.1 |

\* cited by examiner

THERMOCHEMICALLY TREATED MINIATURE TUBES AS SEMIFINISHED PRODUCTS FOR VASCULAR STENTS

CROSS REFERENCE TO RELATED APPLICATIONS

This application claims benefit of priority to U.S. provisional patent application Ser. No. 61/929,985 filed Jan. 22, 2014; the content of which is herein incorporated by reference in its entirety.

TECHNICAL FIELD

The invention relates to a method for increasing the fatigue strength of a tubular semifinished product for a medical implant, a tubular semifinished product for a medical implant having improved fatigue strength, and a medical implant produced from such a semifinfished product.

BACKGROUND OF THE INVENTION

Prior Art

With implants subject to mechanical load, there is a constant need for solutions that lead to an increase of the service life of the implant under mechanical load. For example, stents and cardiac valves are regularly exposed to cyclical mechanical stresses. In order to increase the mechanical load-bearing capacity (and therefore the service life) with these components, one or more of the following measures are carried out in the prior art: coating of final implants with organic and inorganic protective layers in order to increase the degradation resistance (for example galvanic coatings with Zn, coatings based on ionic liquids, conversion coatings by chemical conversion of the main alloy constituents, vaporization or sputtering with Al, thermal spraying, etc.); producing tubular semifinished products from multi-layer composite materials (also in order to increase the radiopacity) by means of plating; use of higher-alloyed starting materials with improved degradation resistance; use of gallium-containing electrolytes in plasma-chemical surface reactions in order to improve the biocompatibility (DE 2009/050048) of absorbable implants; use of gallium-containing lubricants in the high-temperature forming of Mg sleeves; and/orapplication of low-modulus metal coatings in order to increase the ability to plasticize/dilate resorbable stents.

Disadvantages of the Approaches in the Prior Art

Subsequent treatment steps of filigree implants such as stents are disadvantageous in terms of production since the additional handling of the stents in a further process step causes an increased occurrence of mechanical deformations of the components and therefore causes an increased rejection rate.

The advantage of an increased degradation resistance of higher-alloyed starting materials (for example Mg with an alloy content of rare earths$\geq$3%) is often accompanied by disadvantages in terms of the mechanical properties (lower elongation at failure).

In the case of higher-alloyed starting materials, precipitations that are caused by the alloy occur during semifinished product manufacture and may lead to locally inhomogeneous mechanical and chemical property changes. These act as internal notches, which in turn promote the creation of cracks.

Semifinished products produced in the conventional manner (for example by means of plating methods) often demonstrate delaminations of the coating from the main body during the deformation of the end products produced therefrom (for example dilation of stents).

On the basis of the prior art, the object of the present invention was to specify a method for producing semifinished products or implants, such as stents or cardiac valves, which are characterized by improved component properties, such as endurance strength and/or reduced susceptibility to cracks.

In preferred variants, it was also desirable, in the case of degradable metal implant materials, to additionally achieve an improvement of the degradation properties, wherein, here too, the corresponding production method should preferably be simplified and/or accelerated. It was also desirable for preferred variants to achieve an increase in the radiopacity of the implants from the semifinished products to be produced in accordance with the invention.

SUMMARY

The above-stated primary object is achieved in accordance with the invention by a method for increasing the fatigue strength of a tubular semifinished product for a medical implant, the method comprising the following steps:
a) providing the tubular semifinished product; and
b) acting internally on the tubular semifinished product with pressure, such that the outer periphery of the tubular semifinished product is subject to plastic deformation by at least 0.2%.

In some embodiments, the tubular semifinished product consists of metal or a metal alloy. In some embodiments, the semifinished product is for a stent or a cardiac valve.

In some embodiments pressure can be applied by means of a liquid. Fractions of the liquid can be additionally alloyed into the inner surface of the semifinished product. Additional alloying can occur up to at most 50% of the depth of the cross section of the semifinished product. In other embodiments, the pressure is applied by means of metals or metal alloys having a low melting point, optionally selected from the group consisting of liquid Sn, Zn, In, Ga, Li, Na, Bi and alloys thereof.

The invention also includes a tubular semifinished product for a medical implant, wherein internal compressive stresses are present at the inner surface which are at least approximately 15%, optionally selected from the group consisting of 20%, 30%, and 40%, of the proof stress Rp 0.2 established at room temperature in the tensile test and/or are $\geq$20 MPa. The tubular semifinished product for a medical implant can include an additional alloying on its inner face. In some embodiments a medical implant is produced from the semifinished product. The medical implant can be a stent or a cardiac valve.

DETAILED DESCRIPTION OF PREFERRED EMBODIMENTS

Figure 1B:
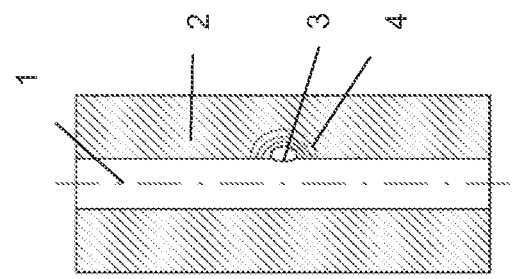
FIGS. 1a and 1b are schematic in cross section form showing a lumen 1, a tube wall 2, a notching 3 in the inner wall; and stress 4 produced due to the notching.

In the context of the present invention, the term "fatigue strength" is to be understood to mean the property of a component (for example a semifinished product or an implant produced therefrom) to resist changing mechanical stresses, wherein these stresses are preferably cyclical. The fatigue strength, in case of doubt, is determined by loading the component in a pulse-like manner (preferably with 100 Hz) and by determining the number of vibrations until the first cracks are produced. This number of vibrations can be established at a specific constant stress level, wherein, of course, the higher the stress level, the lower is the number of established vibrations (number of load alternations) from which the first signs of damage appear. Within the meaning of this text, reference is then made to an increase in the fatigue strength when, for an identical component, a lower number of stress cycles is determined before the method according to the invention is carried out compared to a component after carrying out the method according to the invention, wherein the component was identical to the comparison component before the method according to the invention was carried out.

The proof stress Rp 0.2 constitutes the stress at which a permanent set of 0.2% is achieved. This parameter is established in accordance with ISO 6892-1 or DIN EN ISO 6892-1 in the tension test. The load conditions, produced by the application of internal pressure, of tubes are established by the burst pressure test. This is carried out in accordance with DIN ISO 2758. Here, the material sample is fixed in a circular manner on a membrane, which bends under the action of pressure and causes the material sample to burst. The hydraulic pressure acting on the membrane during the bursting process is the same as the bursting pressure of the material to be examined.

In accordance with the invention, the internal pressure is not increased however to such an extent that the tube bursts. The internal pressure is only increased until a plastic deformation of the tube occurs that causes a permanent increase in diameter or circumference of at least 0.2% of the starting values. For example, the circumference of a tube having the starting outer diameter of 2,000 mm thus increases to 2,004 mm upon reaching the 0.2% proof stress based on the tube geometry. This corresponds to an increase in circumference from 6,283 mm to 6,296 mm. In each case these are the minimum values of the plastic deformations to be implemented. The internal pressure values used here are material-specific in terms of their magnitude, that is to say they are dependent on the strength of the starting material.

By carrying acting internally on the tubular semifinished product with the pressure, internal stress curves produced over the tube cross section are created. These are characterized on the one hand by compressive stresses on the inner face of the tube and on the other hand by tensile stresses on the outer face of the tube. In subsequent processing steps, for example when producing a stent from the tubular semifinished product, the stress gradients can indeed be reduced, but cannot be eradicated completely, such that the remaining internal compressive stresses also improve the fatigue strength of the end products which are produced from the semifinished product produced in accordance with the invention. In particular, this concerns the increase of the endurance strength with cyclical loads, the reduction of the tendency of cracks to spread in zones subject to internal compressive stresses, and additionally leads to larger possible dilation diameters and also to an increase in service life, in particular in the case of implant materials that cannot be degraded, such as the Co—Cr alloy L-605 or the steel alloy 316L. Fortunately, a corresponding internal stress gradient, which causes the increase in the fatigue strength, can also be achieved in degradable materials, such as magnesium alloys, in particular such as WE43 and Z10.

Due to the application of pressure on the inner face of the tube as an additional step in the semifinished product production process, internal compressive stresses are produced on the inner face of the tube, as described, and the level of the stresses decreases to zero as far as the middle of the tube. By contrast, internal tensile stresses are created from the middle of the tube in the direction of the outer faces of the tube. These stresses have their maximum directly at the outer face of the tube. The internal stresses progress in a sinusoidal manner (see FIG. 2).

The fundamental concept of the invention, expressed in a simplified manner, lies in temporarily acting internally on the tubular semifinished product with pressure in such a way that the proof stress Rp 0.2 of the material is exceeded and an internal stress is created in the material.

The internal pressure deformation takes place at pressures which plastically deform the respective tube beyond the proof stress Rp 0.2. Here, a (inner) diameter change (increase) in the range from 0.5% to 1.5% preferably occurs.

Preferred dimensions for the tubular semifinished products to be used in the method according to the invention are as follows:
outer diameter 1-5 mm, preferably 1.2 to 4 mm, more preferably 1.5 to 3 mm and still more preferably 1.8 to 3.5 mm; and/or
wall thickness 0.01 to 1 mm, preferably 0.05 to 0.5 mm and more preferably 0.07 to 0.4 mm; and/or
lengths from 10 to 5000 mm, preferably 50 to 1500 mm and particularly preferably 100 to 2000 mm.

In principle, the semifinished product to be used in the method according to the invention can consist of various base materials, such as plastic, and here in particular polylactide.

The tubular semifinished product preferably consists however of metal or a metal alloy.

Preferred alloys are as follows.

In the field of resorbable magnesium alloys: WE43, AZ31, AZ61, or ZK10.

All of these alloys can be additionally alloyed preferably with up to 1% Ca as required.

In the field of non-resorbable alloys:

Steel 316L (rust- and acid-resistant steel with approximately 16.5-18.5% of Cr; 10.5-13.5% of Ni; 2.0-2.5% of Mo; max. 2.0% of Mn; max. 1.0% of Si; max. 0.07% of C; the rest being formed by Fe);

Cobalt-based alloy L-605 (19-21% of Cr; 14-16% of W; 9-11% of Ni; 1-2% of Mn; max 3% of Fe; the rest being formed by Co);

Cobalt-nickel alloy MP35N (35% of Ni; 20% of Cr; 10% of Mo); or

Nitinol (alloy formed from Ni+Ti) (54.5%-57% of Ni; the rest being formed by Ti).

In the case of metal materials, the effects that can be obtained by the method according to the invention can be achieved particularly well. Besides the increase in the fatigue strength, these effects also include a reduction of the notch sensitivity as a result of the method according to the invention. By introducing internal compressive stresses into the inner surfaces of the tubular semifinished product, the development of notch-induced stress fields in the wall thickness of the tube is thus significantly reduced.

Figure 1A:
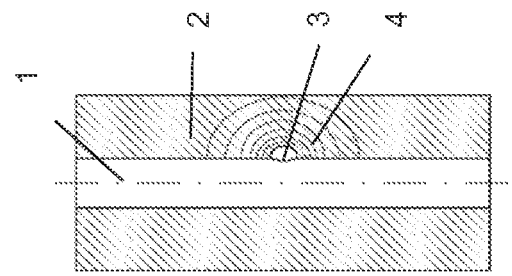

This is illustrated schematically in FIGS. 1a-b, wherein FIG. 1a illustrates a tubular semifinished product produced by a method according to the invention and FIG. 1b illustrates a semifinished product which has not been subjected to the method according to the invention. The reference signs denote the following component parts:

1 lumen
2 tube wall
3 notching in the inner wall
4 stresses produced due to the notching As can be clearly seen from the schematic comparison, the notch stresses in FIG. 1b (tubular semifinished product not produced by the method according to the invention) are much greater.

The described phenomenon is also combined with the fact that there is also an increased tolerance for damage when processing the semifinished product to produce the finished end product. At the same time, there is increased process reliability, since a low probability of fracture during dilation is created by the method according to the invention.

In accordance with the invention, a method wherein the semifinished product is a semifinished product for a stent or for a cardiac valve is preferred.

As already indicated above, these end products can be produced in a particularly high quality by the method according to the invention for the semifinished product.

A further effect can be attained by the application of pressure to the tubular semifinished product from the inside. It is possible, by means of a suitable application of pressure using suitable media, preferably liquids, to attain an additional alloying of the inner surfaces of the tube or an additional alloying of elements or compounds into the tube wall. Here, it is not absolutely necessary for the pressure to be applied such that the semifinished product is deformed above the proof stress Rp 0.2. The latter is a preferred variant however and can therefore be combined well with the method according to the invention.

Accordingly, it is also preferable in a method according to the invention for the pressure to be applied by means of a liquid. This may also be preferred when there is no additional alloying of fractions of the liquid into the surface of the semifinished product, however the variant wherein there is additional alloying into the surface of the semifinished product of fractions of the liquid used to apply pressure is particularly preferred.

An "additional alloying" in the context of the present text is then present if the alloy composition has changed after the "additional alloying" process.

This additional alloying causes a gradual change of the chemical composition over the wall of the tube. This means that the inner wall of the tube experiences the strongest change to the chemical composition, since this is in direct contact with the liquid, for example molten metal or an alloy, of the pressure medium. By contrast, the chemical composition of the middle of the tube and of the outer wall of the tube remains unchanged.

The pressure media vary depending on the property profiles to be set. In the case of the use of L-605, water may be used. If this is pressed into the tube at a pressure for example of approximately 1.500 bar, an internal stress profile with internal compressive stresses on the inner surfaces and internal tensile stresses on the outer surfaces of the tube is created. The internal compressive stresses generate a higher fatigue strength and a lower notch sensitivity of the stent fabricated from the tube when said stent is dilated and then subjected to cyclical load.

In the case of the resorbable materials, it is preferred for a CaZn alloy (having a relatively low melting point, particularly preferably a CaZn alloy with 27 mass % of Zn) to be alloyed in as a result of the application of pressure. This is possible at temperatures≤420° C. both in magnesium surfaces and in the surfaces of tubular semifinished products formed from corroding iron-based alloys or pure iron. By varying the pressure, the residence time of the medium in the interior of the tube, and the temperature, it is possible to produce novel mechanically and chemically functional semifinished products, in particular for stents, using thermochemical methods of this type.

Due to the use of suitable liquid or gaseous carriers as media during the internal pressure deformation process, diffusion effects are generated that lead to a change of the composition of the inner surface of the tubes. The extent achievable here to which the chemical composition of the wall thickness is changed can be varied in wide limits by varying the temperature, the time, the specific pressure curve applied, and the medium.

As a result of the alloying-in due to the application of internal pressure on the inner wall of the tubular semifinished product, a plurality of positive effects (in particular in the method according to the invention), which are partly simultaneously desirable, can be attained as follows.

Additional alloying of the inner surfaces of the tube of metals and alloys that have a functional influence on the degradation processes and biocompatibility. For example, these are magnesium-containing salts, such as magnesium nitrate, which cause an acceleration of the degradation of Fe.

In the case of degradable metal implant materials, both an improvement of the mechanical properties (endurance strength and lower susceptibility to cracks) and an improvement of the degradation properties are attained by additional alloying of the inner surfaces of the stent.

In the case of degradable materials, besides the additional alloying of the inner surface, the setting of defined mechanical properties via the degree of recrystallization (temperature, dwell time) is also possible by application of pressure from the inside by means of molten phases.

In the case of degradable materials, the alloying-in of alloy elements under high pressures causes a considerable acceleration of the diffusion otherwise only controlled by time and temperature. This leads to a much more effective surface-finishing process.

By varying the method parameters (temperature, time), a large spectrum of settable diffusion depths of alloy elements into the base material is produced. In the case of degradable materials, degradation windows variable over time can thus be specified.

An acceleration of the degradation in the case of Fe-based alloys is possible by means of local-element-forming noble metal salts, such as silver chloride (Ts=455° C.), silver bromide (Ts=435° C.), silver iodide (Ts=552° C.). Both a diffusion of the individual elements and also of the compound itself into the Fe bulk takes places at theses temperatures. This leads to an accelerated degradation of the component fabricated therefrom.

Possibilities are provided for improving the biocompatibility of stents by applying more highly compatible materials into the surfaces of base materials that are biocompatible to a lesser extent.

There is a possibility to set differences in the chemical composition of the luminal and abluminal surface.

A delayed degradation of the implants fabricated from the semifinished product (shift of the electrochemical potential) can be achieved.

Due to the use of eutectic alloys as forming medium during the internal pressure deformation process, the possibilities for chemical surface functionalization by diffusion of a plurality of elements into the surfaces of the base material are expanded significantly.

The use of chloride-containing salts (for example MgCl, NaCl), or magnesium nitrate or magnesium nitrate hexahydrate or citric acid, which cause a surface roughening of Fe, a reduction of the corrosion resistance can be produced.

Zinc- and calcium-containing compounds and/or phosphate-containing compounds (for example dipotassium hydrogen phosphate) cause diffusion effects in the magnesium during the process, which leads to the increase of the corrosion resistance (formation of magnesium phosphate close to the surface).

Molten alloys or mixtures of hard salts allow the use of these both as a medium for the internal high-pressure method for introducing the internal stresses and also (or simultaneously) as a medium for the material diffusion effects to be set.

Due to the surface alloying of implant materials with metals that have a lower modulus of elasticity compared to the base material (for example Zn having a modulus of elasticity of 85 GPa compared to Fe with 210 GPa and L-605 with 243 GPa), the risks of the premature creation and development of cracks are reduced.

Possibilities are provided for the simultaneous increase of radiopacity and biocompatibility due to the use of molten eutectic-close binary alloys (for example Pt—Ca).

Accordingly, it is preferred (in particular in the method according to the invention) for the pressure to be applied, in particular to tubes formed from bioresorbable magnesium alloys, by means of metals or metal alloys having a low melting point (Ts≤420° C.), preferably liquid Sn, Zn, In, Ga, Li, Na, Bi and alloys thereof.

A large number of the above-described effects can be achieved in these metals by a person skilled in the art.

Here, it is preferable for additional alloying to occur up to at most 50% of the depth of the cross section of the semifinished product.

This can be controlled well by a person skilled in the art by appropriate application of pressure (pressure, duration, temperature).

In principle, it is possible, due to the application of pressure (in particular in the method according to the invention) to cause elements to diffuse into the wall of the tubular semifinished product, thus leading to a reduction of the degradation rate of resorbable materials, in particular Mg alloys.

In the sense of this description, resorbable materials are materials that can be broken down in the human body without causing damage thereto or that can be converted into compounds that likewise are not harmful to the body.

It is also possible, by means of the application of pressure (in particular in the method according to the invention) to cause an additional alloying of elements in order to accelerate the degradation rate of resorbable alloys, Fe alloys here in particular.

In addition, it is possible (in particular also in the method according to the invention) to attain a combination of improvement of the mechanical properties and of the biological functional properties by alloying suitable elements, depending on the base material, into the walls of the semifinished product by means of an application of pressure in order to reduce the degradation rate (in particular in the case of resorbable magnesium alloys) and in order to accelerate the degradation rate (in particular in the case of resorbable iron alloys). For example, it is thus possible, in the case of implants (in particular stents) produced from these semifinished products, to ensure that precise degradation limits are observed, wherein, as a result of the method according to the invention, the improvement of the fatigue strength and additionally also the improvement of the possibility for plasticizing (which enables a larger dilated diameter, in particular for stents) are to be ensured in parallel.

In accordance with the above, a tubular semifinished product for a medical implant forms part of the invention, wherein internal compressive stresses are present at the inner surface which are approximately 15%, preferably 20%, more preferably 30%, and particularly preferably 40%, of the proof stress Rp 0.2 established at room temperature in the tensile test, and/or wherein internal compressive stresses are ≥20 MPa. An internal compressive stress of ≥30 MPa, more preferably ≥50 MPa and particularly preferably ≥75 MPa, is preferably present on the inner surface.

Although the internal stresses are reduced after laser cutting and electropolishing, they do not revert to zero. Approximately 40 to 50% of the internal stresses present after the application of pressure still remain in the final component. For example, it is thus assumed that a tube formed from a bioresorbable magnesium alloy, such as WE 43, in the untreated state has a proof stress Rp 0.2 of 200 MPa, for example. A tube made of the same alloy and subject internally to an application of pressure has internal compressive stresses on the inner face of the tube of 80 MPa (=40% of the proof stress). After laser cutting and electropolishing, these reduce to approximately 40 MPa (=50% of the internal stresses originally present). These are still sufficient however for the aforesaid property improvements. The proof stress Rp 0.2 is established here in the tensile test according to DIN EN ISO 6892-1.

The internal compressive stresses on the inner face or the inverse internal tensile stresses on the outer face of the tubular semifinished product according to the invention can be established by means of radiographical internal stress analysis. Here, defraction or bending methods are used, for example high-resolution x-ray defractometry (HRXRD) using the inel EQUINOX 6000 apparatus by inel Inc, from Stratham, 03885 NH, USA or the D 5000 x-ray defractomer by Siemens.

Here, deformations caused by an internal stress are established in sub-microscopic regions as lattice expansion of crystalline materials (such as the aforesaid alloys for the implants according to the invention). The present state of internal stress is determined from the measured lattice expansion on the basis of theoretical elasticity relationships. X-ray beams are used to measure the lattice expansion. The advantage of the application of this measurement method lies on the one hand in the freedom from destruction and in the other hand in the high measurement accuracy of +/−1 MPa. In addition, this method is less complex compared to the neutron beam method used alternatively. However, the low penetration depth of the x-ray beams into metal components restricts the use thereof to near-surface areas of a few μm. In order to establish internal stresses at greater component depths, layerby-layer erosion methods are used. In the case of the implant materials and the stents fabricated therefrom, these are preferably electrochemical methods, such as electropolishing. This method ensures that no additional deformations are introduced into the material that would in turn lead to falsified internal stress states. In the case of magnesium alloys, an erosion rate of approximately 10 μm/min is achieved in phosphoric acid-containing electrolyte compositions with application of an anode voltage of approximately 6 V to the components. By applying this method, the respective internal stress state can be established.

However, it must be noted that, in spite of this material erosion carried out with caution, an influence on the equilibrium of forces and moments in the internal stress field is not to be completely ruled out. Mathematical corrections are therefore necessary that determine the internal stress state at the newly created surface in comparison to the component before the erosion. By means of the application of finite element methods (FEMs), these can be calculated depending on the eroded material volume and the component geometry present. However, the measurement accuracy increases to approximately +/−5 MPa.

As already described above, the tubular semifinished products according to the invention are particularly resistant to mechanical loads due to their internal stresses. A tubular semifinished product according to the invention is preferable for a medical implant comprising an additionally alloyed inner face.

Here, this additional alloying can be attained via an application of pressure within the scope of a method according to the invention. This can be determined by a gradient formation, wherein the degree of the additional alloying can be determined by metallographic transverse microsections of which the material composition is scanned in a spatially resolved manner in a scanning electron microscope by means of energy dispersive x-ray analysis. The element mapping created shows the gradients in the chemical composition running over the cross section of the wall of the tube.

In accordance with the above, a preferred tubular semifinished product according to the invention for a medical implant is one that is produced or that can be produced by a method according to the invention.

A medical implant produced from a semifinished product according to the invention also forms part of the invention. Here, the medical implant is preferably a stent or a cardiac valve.

As already described further above, it is possible to attain a sufficiently strong internal stress from the tubular semifinished product according to the invention during the processing to form the implants according to the invention (in particular the preferred implants according to the invention). It is thus possible to also provide these implants with an improved mechanical shelf life.

The fact that a sufficient stress gradient or an internal stress level of approximately 50% of the original internal stress level of the tube to which pressure is applied internally is also maintained after the laser cutting of the tube may preferably be ensured by one or more of the following methods.

Use of ultra-short pulse lasers (for example femtosecond lasers), which produce only a minimal introduction of heat into the tube wall and therefore generate only a minimal heat influence zone at the laser-cut edge.

Very low material removal during the subsequent corroding and electropolishing processes. By way of example, this means that an original tube wall thickness of 90 µm is eroded only to 80 µm and a web width present after the laser cutting process of 100 µm must still be at least 90 µm on the final electropolished stent.

Irrespective of this or even additionally hereto, the above-described advantages can be transferred to the implants according to the invention due to additional alloying by means of application of pressure to the inner wall of the tubular semifinished product.

EXAMPLES

Practical Examples of the Solution According to the Invention

Exemplary pressure values and application times will be specified hereinafter for a few selected tubular semifinished products before specifically describing three practical examples of the invention.

| Material | Pressure medium | Rp 0.2 Proof stress of the initial tube [MPa] | Internal pressure to be applied [bar] | Initial temperature of the pressure medium [° C.] | Dwell time at maximum pressure [s] |
|---|---|---|---|---|---|
| Implant steel 316L | Water | 700 | 1000-1500, preferably 1100 | RT | 5-30, preferably 10-20, particularly preferably 15 |
| Co-based alloy L-605 | Water | 600 | 800-1400, preferably 1000 | RT | 5-30, preferably 10-20, particularly preferably 15 |
| Magnesium alloy WE 43 | Ca—Zn alloy (73% Ca, 27% Zn) | 200 | 100-200, preferably 150 | 380-450, preferably 410 | 600-1200, preferably 700-1000, particularly preferably 800 |
| Pure iron | Magnesium nitrate hexahydrate $Mg(NO_3)_2 \cdot 6H_2O$ | 200 | 150-200, preferably 175 | 80-120, preferably 100 | 600-1200 preferably 700-1000 particularly preferably 800 |

1.) L-605 (Tube formed from CoCr alloy)

A tube made of a CoCr alloy has the following alloy composition (% by weight):
19-21% of Cr
14-16% of W
9-11% of Ni
1-2% of Mn
max 3% of Fe
the rest being formed by Co.

This tube has a length of 2 m and an outer diameter of 2.00 mm with a wall thickness of 0.10 mm. The Rp 0.2 proof stress of the initial tube is 600 MPa. By means of an application of pressure internally with water of originally 20° C. at 1.000 bar, this tube is plastically deformed over a period of time of 15 s just above the proof stress. The outer diameter increases here to 2.01 to 2.02 mm. This means that the material has been deformed above the Rp 0.2 proof stress. This means that the permanent set is approximately 1%. The internal compressive stresses created here directly at the inner surface of the tube reach values of 500 MPa. The internal tensile stresses at the outer surface of the tube reach 500 MPa (see FIG. 2).

During the subsequent laser cutting and the corroding and electropolishing processes in mineral acid mixtures, the internal compressive and tensile stresses are reduced to approximately 50%. The final stent now has an outer diameter range between 2.00 and 2.01 mm. This means that 5 µm have been removed internally and 5 µm have been removed externally from the two sides of the tube wall in each case. On the whole, the outer diameter reduces by 10 µm and the inner diameter increases by 10 µm compared to the tube to which pressure is applied internally. The remaining internal compressive stresses of the inner surfaces of the stent now present are now between 200 and 250 MPa. The resultant increased fatigue strength increases the cycles of limit load stressing by 25% compared to stents made of untreated tube.

2.) Tubes Made of the Mg Alloy WE 43

This alloy consists of 4% by weight of Y and 3% by weight of rare earths (Nd, Dy, Gd) and approximately 0.5% by weight of Zr, the rest being formed by Mg.

This tube has a length of 2 m and an outer diameter of 2.00 mm with a wall thickness of 0.18 mm. The Rp 0.2 proof stress of the initial tube is 200 MPa. A molten alloy formed from 27% of Zn and 73% of Ca is pressed at 410° C. with a pressure of 150 bar into an Mg tube. The duration of the application of pressure to the tube by means of the molten medi-µm is 10 to 20 min. The inner surface is additionally alloyed with Ca and Zn up to a depth of 30 µm by diffusion effects. The wall thickness thus increases from 180 µm to now 190 µm. Of the 30 µm of additionally alloyed inner wall of the tube, approximately 10 µm are removed again by corrosion and polishing during the stent manufacturing process. The erosion of the outer wall, which is not additionally alloyed, is likewise approximately 10 µm. A stent wall thickness of 170 µm thus remains. The permanent internal compressive stress level at the inner face of the stent lies in the region of 80 MPa.

The final, finished processed stent has an outer diameter of 1.98 mm. The permanent additionally alloyed zone, 20 µm thick, of the inner wall of the tube leads to a degradation time that is extended by approximately four weeks compared to a stent made of untreated starting material. This treatment also leads to an increase of the maximum dilated diameter by 0.3 mm to now 4.8 mm before the first web fracture occurs. Stents that do not experience a treatment of this type by contrast exhibit their first web fractures at just 4.5 mm.

3.) Cobalt Chromium Alloy MP 35 N

A tube formed from a CoNi alloy has the following alloy composition (% by weight):
34-36% of Ni
18-21% of Cr
9-11% of Mo
the rest being formed by Co.

This tube has a length of 2 m and an outer diameter of 1.80 mm with a wall thickness of 0.09 mm. The Rp 0.2 proof stress of the initial tube is 1.000 MPa. As a result of an application of pressure internally by means of water of originally 20° C. at 1.300 bar, this tube is plastically deformed just above the proof stress over a period of time of just 10 s. The outer diameter increases to 1.81 to 1.82 mm. This means that the material has been deformed just above the Rp 0.2 proof stress. This means that the permanent set is approximately 1%. The internal compressive stresses created here directly at the inner surface of the tube reach values of 600 MPa. The internal tensile stresses on the outer surface of the tube reach 600 MPa (see FIG. 2).

During the subsequent laser cutting and the corroding and electropolishing processes in mineral acid mixtures, the internal compressive and tensile stresses are reduced to approximately 50%. The final stent now has an outer diameter range between 1.78 and 1.79 mm. This means that 5 µm have been removed internally and 10 µm have been removed externally from both sides of the tube wall in each case. On the whole, the outer diameter reduces by 20 µm and the inner diameter increases by 10 µm with respect to the tube to which pressure is applied internally. The permanent internal compressive stresses of the inner surfaces of the stent now present are now between 250 and 300 MPa. The resultant increased fatigue strength increases the cycles of limit load stressing by 25% compared to stents made form an untreated tube.

Figure 2:
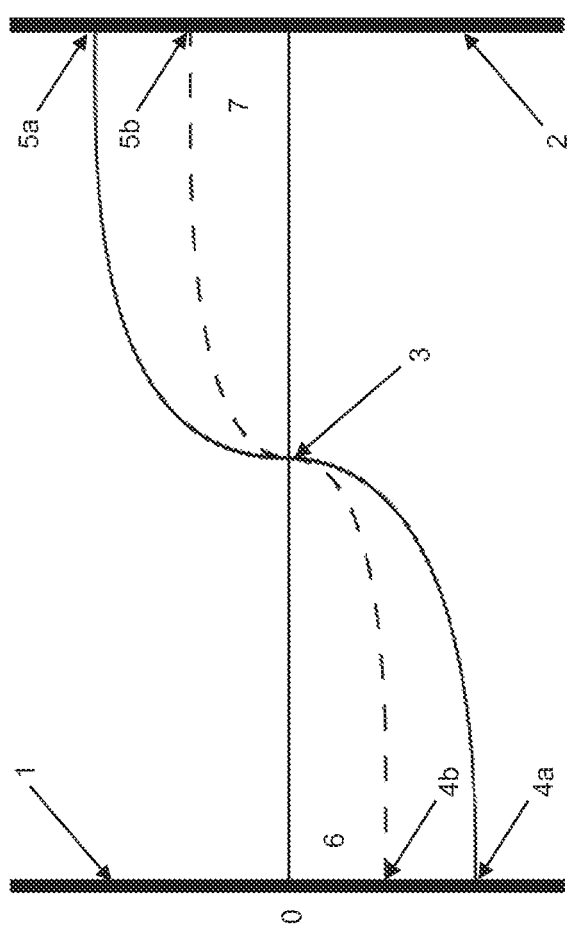
FIG. 2 is a schematic illustrating the course of the internal stresses from the inner face of the tube to the outer face of the tube.

FIG. 2 schematically illustrates the course of the internal stresses from the inner face of the tube to the outer face of the tube.

Here, the reference signs have the following meanings
1 inner face of the tube
2 outer face of the tube
3 middle of the tube wall
4a scale value for the maximum compressive stress at the inner face of the tube to which pressure is applied internally
4b scale value for the maximum compressive stress at the inner face of the stent
5a scale value for the maximum tensile stress at the outer face of the tube to which pressure is applied internally
5b scale value for the maximum tensile stress at the outer face of the stent
6 compressive stress curve
7 tensile stress curve After the application of pressure internally, the stress curve illustrated by the solid line is produced, which creates an initial maximum compressive stress of 500 MPa on the inner face of the tube and an initial maximum tensile stress of 500 MPa on the outer face of the tube. The surface integrals produced above and below the stress-free zero line are of equal magnitude.

Due to the mass removal implemented during the stent production and the resultant reduction of the wall thicknesses, the internal stress level is also reduced. The dashed curve in FIG. 2 constitutes the internal stress state from the inner face of the web to the outer face of the web. In principle, a reduction of the respective internal stress level to or by 50% from the state of the tube to which pressure is applied internally can be observed.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A method for increasing the fatigue strength of a tubular semifinished product for a medical implant, the method comprising the following steps:
   a) providing a tubular semifinished product comprising a continuous solid wall;
   b) applying pressure internally to the tubular semifinished product at room temperature to plastically deform the tubular semifinished product such that an inner diameter of the tubular semifinished product is increased from 0.5% to 1.5%; and
   c) forming a stent or a cardiac valve from the plastically deformed semifinished product.

2. The method as claimed in claim 1, wherein the tubular semifinished product consists of metal or a metal alloy.

3. The method as claimed in claim 1, wherein the pressure is applied by means of a liquid.

4. The method as claimed in claim 1, wherein the step of forming the stent or the cardiac valve from the semifinished product comprises laser cutting the product to form a stent.

5. The method as claimed in claim 4, wherein the laser applies short pulses to generate minimal heat at a laser cut edge.

6. The method as claimed in claim 1, wherein the plastic deformation results in a sinusoidal stress gradient across the semi-finished product characterized by an increased compressive stress on an internal surface of the semifinished product, an increased tensile stress on an exterior surface of the semi-finished product and an unchanged stress at about the middle of the semi-finished product.

* * * * *